United States Patent [19]

Hunton

[11] 4,400,569

[45] Aug. 23, 1983

[54] METHOD AND APPARATUS FOR DEHYDROGENATION OF ALKYLAROMATIC COMPOUNDS TO PRODUCE VINYLAROMATIC MONOMERS

[75] Inventor: Thomas M. Hunton, Big Spring, Tex.

[73] Assignee: Cosden Technology, Inc., Dallas, Tex.

[21] Appl. No.: 315,428

[22] Filed: Oct. 27, 1981

[51] Int. Cl.$^3$ .......................... C07C 5/36; C07C 5/38; C07C 5/40

[52] U.S. Cl. .................................. 585/444; 585/441; 585/445

[58] Field of Search ........................ 585/444, 445, 441

[56] References Cited

U.S. PATENT DOCUMENTS

| | | | |
|---|---|---|---|
| 2,401,846 | 6/1946 | Sumerford | 585/444 |
| 2,402,740 | 6/1946 | Doumani et al. | 585/444 X |
| 2,405,436 | 8/1946 | Laughlin | 585/444 |
| 2,414,585 | 1/1947 | Eggertsen et al. | 585/444 |
| 3,387,053 | 6/1968 | Lee | 585/444 X |
| 3,502,737 | 3/1970 | Ghublikian | 585/444 X |
| 3,636,183 | 1/1972 | Pasternak et al. | 585/444 X |
| 3,652,698 | 3/1972 | Benslay et al. | 585/444 X |
| 3,787,188 | 1/1974 | Lyon | 585/444 X |
| 3,870,764 | 3/1975 | Gichowski et al. | 585/444 X |
| 3,907,916 | 9/1975 | Soderquist et al. | 585/444 X |
| 4,039,601 | 8/1977 | Soderquist et al. | 585/444 X |
| 4,165,441 | 8/1979 | Okano et al. | 585/444 |
| 4,229,603 | 10/1980 | Lyon | 585/444 |
| 4,287,375 | 9/1981 | Möller et al. | 585/444 X |

*Primary Examiner*—Paul F. Shaver
*Attorney, Agent, or Firm*—Schwartz, Jeffery, Schwaab, Mack, Blumenthal & Koch

[57] ABSTRACT

A method of dehydrogenating alkylaromatic compounds to produce vinylaromatic monomers wherein an alkylaromatic compound feed stream is preheated by passing it in indirect heat exchange relation with steam, the preheated feed stream is then flash vaporized by injecting superheated steam therein, the feed vapors are then passed in indirect heat exchange relation with hot effluent vapors withdrawn from the dehydrogenation reaction zone, after which the hot alkylaromatic compound vapors are introduced, together with superheated steam into a dehydrogenation reaction zone containing a bed of alkylaromatic compound dehydrogenation catalyst and reacted to produce a vinylaromatic compound containing effluent stream which is withdrawn from the reaction zone, passed in heat exchange relation with the incoming alkylaromatic compound feed and condensed. The resulting condensate is separated into an aqueous phase and a crude vinylaromatic compound containing organic phase which can be purified by subsequent distillation; and apparatus for carrying out the described method.

29 Claims, 1 Drawing Figure

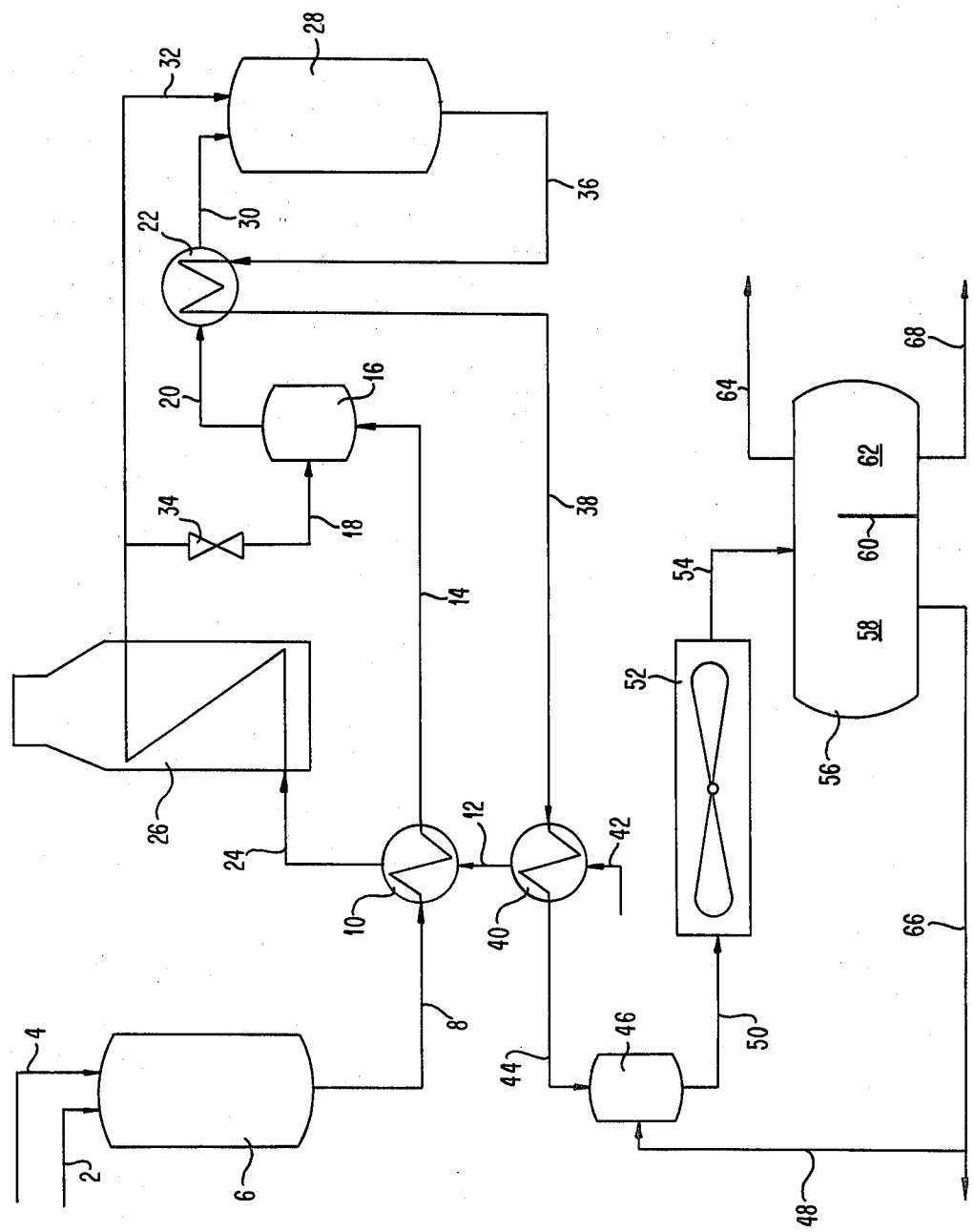

METHOD AND APPARATUS FOR DEHYDROGENATION OF ALKYLAROMATIC COMPOUNDS TO PRODUCE VINYLAROMATIC MONOMERS

BACKGROUND OF THE INVENTION

This invention relates to catalytic dehydrogenation of alkylaromatic compounds to produce vinylaromatic compounds. More particularly, this invention relates to a method and apparatus in which the alkylaromatic feed is first vaporized and then passed in heat exchange relation with effluent gases from the dehydrogenation zone before the feed is introduced into the dehydrogenation zone. Specifically, this invention relates to a method and apparatus for producing vinylaromatic monomers by catalytic dehydrogenation of alkylaromatic compounds wherein the alkylaromatic feed is flash vaporized.

Vinylaromatic compounds such as styrene, vinyltoluene, alpha-methylstyrene, divinylbenzene and the like are important as monomers from which useful polymers are made. These monomers are typically produced by catalytic dehydrogenation of alkylaromatic compounds to the corresponding vinylaromatic compounds in the presence of steam at elevated temperatures. Before the alkylaromatic feed is introduced into the dehydrogenation zone, it is typically preheated by first passing it in indirect heat exchange relation with steam and thereafter passing it in indirect heat exchange relation with hot effluent gases withdrawn from the dehydrogenation zone.

Although some vaporization of the alkylaromatic feed may take place during the initial heat exchange operation with steam, vaporization of the feed occurs primarily in the feed/effluent heat exchanger. Generally, the feed comprises, in addition to the desired alkylaromatic compound, minor proportions of vinylaromatic compound. This creates a problem in the feed/effluent heat exchanger because the alkylaromatic compound tends to vaporize first, leaving behind a liquid phase with an enriched content of vinylaromatic compound. These vinylaromatic compounds are highly reactive and tend to polymerize in the liquid phase at temperatures encountered in the feed/effluent heat exchanger. The preferential evaporation of alkylaromatic compound and resulting enrichment of the remaining liquid phase in vinylaromatic compound increases the likelihood that vinylaromatic compound molecules in the liquid phase will encounter each other and polymerize. As a result, vinylaromatic polymer deposits form in the feed/effluent heat exchanger. Polymerization occurs when liquid phase material containing an enriched amount of vinylaromatic compound contacts the hot tube walls of the feed/effluent heat exchanger which typically have a temperature lying in the range from about 500 to about 600 degrees C.

Carbonaceous deposits which progressively accumulate on the catalyst in the dehydrogenation zone may be removed by periodic steaming of the catalyst. Such treatments, however, do nothing to ameliorate the formation of polymer and/or coking of the feed/effluent heat exchanger. After a period of operation, it becomes necessary to take the feed/effluent heat exchanger out of service for cleaning. As a result, the cost of producing vinylaromatic monomers is increased both by the increased operating cost attributable to the cleaning operation and by the loss in productivity of the equipment.

The problem of polymer formation and coking in the inlet system leading to the dehydrogenation reactor is particularly severe in the dehydrogenation of ethyltoluene to produce vinyltoluene. When ethyltoluene is being dehydrogenated to produce vinyltoluene, it is necessary to clean the heat exchanger at from 1 to 6 month intervals.

OBJECTS OF THE INVENTION

Accordingly, it is an object of the present invention to provide an improved method and apparatus for catalytic dehydrogenation of alkylaromatic compounds to produce vinylaromatic compounds in which, prior to being introduced into the dehydrogenation reactor, the alkylaromatic feed is passed in heat exchange relation with effluent gases withdrawn from the dehydrogenation reactor.

Another object of the present invention is to provide a method and apparatus for dehydrogenating alkylaromatic compounds in which the formation of a liquid phase containing an enriched amount of vinylaromatic compound is prevented during vaporization of the alkylaromatic compound feed.

A further object of the present invention is to provide a method and apparatus for dehydrogenation of alkylaromatic compounds which assures complete vaporization of the alkylaromatic compound feed before introduction of the feed into the dehydrogenation zone.

It is also an object of the present invention to provide a method and apparatus for catalytic dehydrogenation of alkylaromatic compounds to produce vinylaromatic compounds in which the production equipment may be run for a longer period before it must be shut down for cleaning.

Yet another object of the present invention is to provide a method and apparatus of the aforedescribed type in which the tendency of carbonaceous deposits to build up in the feed/effluent heat exchanger is markedly reduced.

A still further object of the present invention is to provide an apparatus for catalytic dehydrogenation of alkylaromatic compounds to produce vinylaromatic compounds in which the feed/effluent heat exchanger is less prone to fouling.

An additional object of the present invention is to provide a method and apparatus which enable more economical production of vinylaromatic compounds from alkylaromatic compounds by catalytic dehydrogenation.

A still further object of the present invention is to provide a method and apparatus for catalytic dehydrogenation of alkylaromatic compounds to produce vinylaromatic compounds which reduces the down time and increases the productivity of the production equipment.

It is a particular object of the present invention to provide a method and apparatus which is especially applicable to catalytic dehydrogenation of ethyltoluene to produce vinyltoluene.

SUMMARY OF THE INVENTION

These and other objects of the invention are achieved by providing a method for catalytically dehydrogenating alkylaromatic compounds to produce vinylaromatic monomers comprising flash vaporizing an alkylaromatic compound stream, introducing the vaporized alkylaromatic compound and superheated steam into a dehydrogenation zone containing a bed of alkylaromatic compound dehydrogenation catalyst at an elevated temperature sufficient to induce catalytic dehydrogenation, and withdrawing vinylaromatic compound containing effluent gases from said dehydrogenation zone.

The objects of the invention are further achieved by providing apparatus for catalytically dehydrogenating alkylaromatic compounds to produce vinylaromatic monomers comprising reaction zone means containing a bed of alkylaromatic compound dehydrogenation catalyst, means for introducing a flow of alkylaromatic compound into said reaction zone means, means for introducing superheated steam into said reaction zone means, means for withdrawing effluent gases from said reaction zone means, and means for flash vaporizing said flow of alkylaromatic compound prior to introducing said alkylaromatic compound into said reaction zone means.

In further preferred aspects of the invention, the flash vaporization of the alkylaromatic compound is effected by diverting a portion of the superheated steam flowing through a steam inlet line leading to the reaction zone and injecting the diverted superheated steam directly into the alkylaromatic compound stream; the alkylaromatic compound stream is preheated by passing it in indirect heat exchange relation with steam prior to vaporizing the alkylaromatic compound; the vaporized alkylaromatic compound is passed in indirect heat exchange relation with hot effluent gases withdrawn from the dehydrogenation reaction zone, and steam from the preheat heat exchanger is conveyed to a boiler and superheated to provide superheated steam for the flash vaporization and the catalytic dehydrogenation.

BRIEF DESCRIPTION OF THE DRAWINGS

The invention will be explained in further detail with reference to the accompanying FIGURE which is a schematic representation of an installation for producing vinylaromatic compounds by catalytic dehydrogenation of the corresponding alkylaromatic compounds according to the invention.

DETAILED DESCRIPTION OF PREFERRED EMBODIMENTS

The invention will be described hereinafter with reference to a system for producing vinyltoluene by catalytic dehydrogenation of ethyltoluene. It is understood, however, that the process and apparatus of the invention are also applicable to the production of other vinylaromatic monomers such as styrene, alpha-methylstyrene, divinylbenzene and the like. It is considered within the skill of the art to adjust the operating parameters as necessary to adapt the system to other vinylaromatic monomers.

Referring now to the drawing, the FIGURE represents a system for producing vinyltoluene. Toluene and ethylene are introduced through lines 2 and 4 respectively into an alkylation reactor 6 where the toluene is alkylated by the well known Friedel-Crafts reaction to produce ethylbenzene. Known Friedel-Crafts catalysts such as aluminum trichloride ($AlCl_3$) activated with hydrogen chloride (HCl) or ethyl chloride ($CH_3CH_2Cl$) may be used. The resulting is conveyed from alkylation reactor 6 through line 8 to a heat exchanger 10 where it is preheated by passing it in indirect heat exchange relation with steam from line 12. Generally the ethyltoluene feed is preheated to a temperature lying in the range from about 120 degrees C. to about 150 degrees C.

The ethyltoluene feed then passes through line 14 to a flash vaporization zone 16 where superheated steam from line 18 is injected into the alkylaromatic compound stream. The direct contact heat transfer between the superheated steam and the alkylaromatic feed causes the alkylaromatic feed to be vaporized substantially instantaneously. All of the feed stream vaporizes including any vinyltoluene present therein. Consequently, no liquid phase having an enriched content of vinyltoluene is allowed to form and subsequent formation of vinyltoluene oligomers in the supply lines leading to the dehydrogenation reactor is greatly reduced.

The ethyltoluene vapors then pass through line 20 to a feed/effluent heat exchanger 22 where the vapors are further heated by passing them in heat exchange relation with the hot effluent from the dehydrogenation reactor. The steam from preheater heat exchanger 10 passes through line 24 to a heater or boiler 26 where it is superheated. The temperature of the superheated steam produced in heater 26 preferably ranges between about 700 degrees C. and about 760 degrees C. The hot ethyltoluene vapors from feed/effluent heat exchanger 22 then pass to a dehydrogenation reactor 28 through line 30. The rate at which ethyltoluene vapors are introduced into the dehydrogenation reactor generally ranges from a liquid hourly space velocity of about 0.4 to about 0.8. Superheated steam from heater 26 is also passed to dehydrogenation reactor 28 through line 32. A portion of the superheated steam from line 32 is diverted through line 18 to flash vaporization zone 16. Valve 34 is provided on line 18 to regulate the flow of steam to the flash vaporizer.

Dehydrogenation reactor 28 contains a bed of an alkylaromatic compound dehydrogenation catalyst. Generally, the catalyst is a base metal catalyst in solid granular form. Typical alkylaromatic compound dehydrogenation catalysts are promoted iron oxide catalysts. Numerous suitable catalysts are commercially available. For example, suitable catalysts include Shell-105, Shell-015, United-G64A, United-G64C or United-G64D. Temperatures within the dehydrogenation reactor range between about 550 degrees C. and about 700 degrees C., preferably between about 560 degrees C. and about 650 degrees C.

The proportions of steam and ethyltoluene introduced into the dehydrogenation reactor may range from about 1 to about 10 parts by weight steam per part ethyltoluene which corresponds to a mole ratio of steam to hydrocarbon from about 7.5 to 1 to about 75 to 1. Preferably the weight ratio of steam to ethyltoluene is from about 2 to about 4 parts by weight steam per part of ethyltoluene which corresponds to a molar ratio of steam to hydrocarbon between about 15 to 1 and about 30 to 1. Most preferably, the molar ratio of steam to ethyltoluene is at least about 22.5 to 1.

The effluent vapors leaving dehydrogenation reactor 28 comprise a mixture of steam, vinyltoluene, hydrogen gas, some undehydrogenated ethyltoluene and minor amounts of other alkylaromatics. The effluent vapors pass through line 36 to feed/effluent heat exchanger 22 where a portion of their heat is transferred to the ethyltoluene vapor feed.

The temperature prevailing in the feed/effluent heat exchanger depends on the temperature of the effluent gases withdrawn from the dehydrogenation zone. Desirably, the temperature of the effluent gases will be less than about 700 degrees C. preferably less than about 650 degrees C., and the temperature of the hot side of the heat exchanger will be between about 500 degrees C. and about 600 degrees C. If the temperature of the effluent gases exceeds this level, it may indicate that the temperature prevailing in the dehydrogenation reaction zone is too high. Excessively high operating temperatures in the dehydrogenation zone should be avoided since they may damage the catalyst. Excessively high temperatures in the feed/effluent heat exchanger may increase the formation of undesired coke deposits.

From heat exchanger 22, the product vapors pass through line 38 to another heat exchanger 40 where more of their heat is transferred to steam entering through line 42. The partially cooled vapors then pass through line 44 to a quench zone 46 where they are quenched with a stream of water entering through line 48. The quenched product passes from quench zone 46 through line 50 to a condenser, such as air cooler 52, where the product stream is finally cooled to a temperature between about 15 degrees C. and about 75 degrees C. and condensation of the water and hydrocarbon is completed.

The condensate from air cooler 52 passes through line 54 to a separating drum 56. The hydrocarbon constituents of the product stream separate from the aqueous constituents in chamber 58 and the organic phase flows over the top of weir 60 into chamber 62. Uncondensed gases such as hydrogen are withdrawn from separator 56 through line 64. The aqueous phase of the condensate is withdrawn from the bottom of chamber 58 through line 66. A portion of the water passing through line 66 may be diverted through line 48 for introduction into quench zone 46. The remaining water from line 66 may advantageously be conveyed to the boilers which produce steam for use in the system. The crude vinyltoluene is withdrawn from chamber 62 of separator 56 through line 68 to a purification stage such as a conventional distillation train (not shown).

By virtue of the present invention, complete vaporization of the alkylaromatic feed is achieved without temporary formation of an enriched vinylaromatic compound containing liquid phase which may polymerize in the heat/effluent heat exchanger or other parts of the feed system. Fouling and coking of the feed system are thus prevented, the run times of the system are extended, and more economical production of vinylaromatic monomers is achieved.

Reduced coking of the feed system may also result from the fact that some of the superheated steam may react with carbonaceous residues forming in the feed system via the water-gas reaction thereby consuming such residues and preventing the residues from accumulating.

Other techniques of flash vaporizing the alkylaromatic feed stream may also be utilized. For example, the feed stream could be flash vaporized by subjecting the feed stream to high pressure, increasing the temperature of the feed stream and then rapidly introducing the feed stream into a zone of lower pressure.

Further aspects of the invention will appear from a consideration of the following non-limiting example.

EXAMPLE 1

Ethyltoluene and superheated steam are continuously introduced into a dehydrogenation reactor containing a bed of Shell-105 dehydrogenation catalyst, and a vinyltoluene containing effluent gas stream is withdrawn from the reaction zone. The ethyltoluene feed is passed through a shell and tube heat exchanger in heat exchange relation with the hot effluent gases withdrawn from the reaction zone before being introduced into the dehydrogenation reactor. The temperature of the superheated steam is approximately 725 degrees C. The ethyltoluene is preheated by passing it in indirect heat exchange relation with steam and then vaporized by injecting superheated steam into the ethyltoluene stream prior to passing it to the feed/effluent heat exchanger. The rate at which ethyltoluene is fed to the dehydrogenation zone is controlled to maintain a liquid hourly space velocity of approximately 0.6. The rate at which steam is introduced was controlled to maintain a molar ratio of steam to hydrocarbon of approximately 25 to 1. The temperature of the effluent gases withdrawn from the dehydrogenation reaction zone is approximately 650 degrees C.

After 150 days of operation in this manner, the feed/effluent heat exchanger is taken out of service and inspected. Only negligible coking of the heat exchanger is observed indicating that continued operation would be possible. In contrast thereto, after a similar period of conventional operation during which superheated steam is not injected into the ethyltoluene stream to flash vaporize the ethyltoluene prior to passage through the feed/effluent heat exchanger, the heat exchanger is generally so fouled with carbonaceous deposits, that cleaning of the exchanger is necessary before operation of the system can be resumed.

The foregoing embodiments have been described merely to illustrate the invention and are not intended to be limiting. Since modifications of the described embodiments incorporated the spirit and substance of the invention may occur to persons skilled in the art, the scope of the invention is to be limited solely by the scope of the appended claims.

I claim:

1. A method for catalytically dehydrogenating alkylaromatic compounds to produce vinylaromatic monomers comprising:
    flash vaporizing an alkylaromatic compound stream;
    subsequently introducing the flash vaporized alkylaromatic compound and superheated steam into a dehydrogenation zone containing a bed of alkylaromatic compound dehydrogenation catalyst at an elevated temperature sufficient to induce catalytic dehydrogenation; and
    withdrawing vinylaromatic compound containing effluent gases from said dehydrogenation zone.

2. A method according to claim 1 wherein said flash vaporization is effected by injecting superheated steam into said alkylaromatic compound stream.

3. A method according to claim 1 wherein said alkylaromatic compound stream is preheated prior to said flash vaporization thereof.

4. A method according to claim 3 wherein said preheating is effected by passing said alkylaromatic compound stream in indirect heat exchange relation with steam.

5. A method according to claim 3 wherein said alkylaromatic compound stream is preheated to a temperature lying in the range from about 120 degrees C. to about 150 degrees C.

6. A method according to claim 4 wherein said steam is thereafter conveyed to a boiler and superheated.

7. A method according to claim 6 wherein at least a portion of said superheated steam is injected into said alkylaromatic compound stream to effect flash vaporization of said alkylaromatic compound.

8. A method according to claim 6 wherein at least a portion of said superheated steam is introduced into said dehydrogenation zone.

9. A method according to claim 1 wherein said vaporized alkylaromatic compound is passed through a heat exchanger in indirect heat exchange relation with effluent gases withdrawn from said dehydrogenation zone before said vaporized alkylaromatic compound is introduced into said dehydrogenation zone.

10. A method according to claim 1 wherein said alkylaromatic compound is introduced into said dehydrogenation zone at a liquid hourly space velocity from about 0.4 to about 0.8.

11. A method according to claim 2 wherein from about 3 to about 9 parts superheated steam per part alkylaromatic compound by weight are injected into said alkylaromatic compound stream.

12. A method according to claim 1 wherein said alkylaromatic compound stream comprises a minor proportion of vinylaromatic compound.

13. A method according to claim 1 wherein the molar ratio of superheated steam to alkylaromatic compound introduced into said dehydrogenation zone lies in the range from about 15 to 1 to about 30 to 1.

14. A method according to claim 13 wherein the molar ratio of steam to alkylaromatic compound is at least about 22.5 to 1.

15. A method according to claim 2 wherein the superheated steam injected into said alkylaromatic compound stream is obtained by diverting a portion of the superheated steam introduced into said dehydrogenation zone.

16. A method according to claim 1 further comprising condensing the effluent gases withdrawn from said dehydrogenation zone, separating the resulting condensate into an aqueous liquid phase and a vinylaromatic compound containing organic liquid phase, and recovering the vinylaromatic compound containing organic phase.

17. A method according to claim 16 further comprising recovering said aqueous liquid phase and using said aqueous liquid to generate steam for use in the reaction system.

18. A method according to claim 16 further comprising recovering said aqueous liquid phase and quenching effluent gases withdrawn from said dehydrogenation zone by injecting at least a portion of said recovered aqueous liquid into said effluent gases.

19. A method according to claim 1, wherein said vinylaromatic compound is selected from the group consisting of styrene, vinyltoluene, alpha-methylstyrene and divinylbenzene.

20. A method according to claim 19, wherein said alkylaromatic compound is ethylbenzene and said vinylaromatic compound is styrene.

21. A method according to claim 19, wherein said alkylaromatic compound is ethyltoluene and said vinylaromatic compound is vinyltoluene.

22. A method according to claim 1, wherein said elevated temperature lies in the range from about 550 degrees C. to about 700 degrees C.

23. A method according to claim 22, wherein said elevated temperature lies in the range from about 560 degrees C. to about 650 degrees C.

24. A method according to claim 1, wherein the temperature of superheated steam lies in the range from about 700 degrees C. to about 760 degrees C.

25. A method according to claim 1, wherein said dehydrogenation catalyst is a promoted iron oxide catalyst.

26. A method according to claim 1, wherein the temperature of the effluent gases withdrawn from said dehydrogenation zone is less than about 700 degrees C.

27. A method according to claim 26, wherein the temperature of said effluent gases withdrawn from said dehydrogenation zone is less than about 650 degrees C.

28. A method according to claim 9, wherein said heat exchanger is a shell and tube heat exchanger.

29. A method according to claim 9, the temperature prevailing in said heat exchanger lies in the range from about 500 degrees C. to about 600 degrees C.

* * * * *